United States Patent
Garcia et al.

[11] Patent Number: 5,950,877
[45] Date of Patent: Sep. 14, 1999

[54] FLUID DISPENSING PUMP HAVING BACTERIOSTATIC SUBSTANCE IN PUSHBUTTON

[75] Inventors: Firmin Garcia, Evreux; Olivier Fourment, Paris; Guillaume Brouet, Rouen; Laurent Arghyris, Sotteville-les-Rouen, all of France

[73] Assignee: Valois S.A., Le Neubourg, France

[21] Appl. No.: 08/981,851
[22] PCT Filed: Jul. 5, 1996
[86] PCT No.: PCT/FR96/01048
§ 371 Date: Apr. 22, 1998
§ 102(e) Date: Apr. 22, 1998
[87] PCT Pub. No.: WO97/02900
PCT Pub. Date: Jan. 30, 1997

[30] Foreign Application Priority Data

Jul. 7, 1995 [FR] France ................................ 95/08263

[51] Int. Cl.[6] ........................................ B67D 5/58
[52] U.S. Cl. ........................... 222/190; 222/321.2
[58] Field of Search ......................... 222/190, 321.2, 222/547

[56] References Cited

U.S. PATENT DOCUMENTS

| | | |
|---|---|---|
| 4,801,093 | 1/1989 | Brunet et al. |
| 5,105,993 | 4/1992 | LaHaye et al. ............... 222/189 |
| 5,373,972 | 12/1994 | Bystrom et al. ............. 222/212 |
| 5,490,938 | 2/1996 | Sawan et al. ................ 210/651 |

FOREIGN PATENT DOCUMENTS

| | | |
|---|---|---|
| 473 892 | 3/1992 | European Pat. Off. . |
| 534 088 | 3/1993 | European Pat. Off. . |
| 580 460 | 6/1993 | European Pat. Off. . |
| 28 30 977 | 1/1980 | Germany . |

Primary Examiner—Gregory L. Huson
Attorney, Agent, or Firm—Sughrue, Mion, Zinn, Macpeak & Seas, PLLC

[57] ABSTRACT

A device for dispensing a fluid and operating without air intake, the device comprising a pump (1) mounted on a receptacle (3) containing the fluid, and a pushbutton (10) for actuating said pump, said pushbutton (10) including a fluid dispensing orifice (17), a substance having bacteriostatic activity on said fluid when it comes into contact with said substance being disposed in said dispenser device, the device being characterized in that said pushbutton (10) includes a nozzle (11) defining an expulsion channel (13) that is narrow and of small volume between the pump (1) and the dispensing orifice (17), said substance having bacteriostatic activity being disposed solely in said pushbutton (10) on or in the vicinity of said nozzle (11) such that said substance having bacteriostatic activity is of maximum effectiveness because of the small dead volume in the pushbutton.

6 Claims, 1 Drawing Sheet

FLUID DISPENSING PUMP HAVING BACTERIOSTATIC SUBSTANCE IN PUSHBUTTON

BACKGROUND OF THE INVENTION

The present invention relates to a device for dispensing a-fluid having bacteriostatic activity.

It is known to use heavy metals, such as silver, alloys thereof, or salts thereof as a substance having bacteriostatic or oligodynamic activity, i.e. a disinfectant for fluids. Silver is soluble in water at ppb concentrations, and silver ions delivered in this way act in bacteriostatic and bactericidal manner on germs that have penetrated into the fluid, thereby eliminating them.

Document EP-0 473 892 discloses a metering pump without air intake having an oligodynamic substance disposed at the admission valve of the pump chamber. Additionally, the oligodynamic substance may also be disposed in other parts of the metering pump. As described in document EP-0 473 892, the purpose of that device is to guarantee particularly effective elimination of germs. That purpose is achieved by providing prolonged contact between the liquid and the oligodynamic substance. By having said substance present at the inlet valve to the pump chamber, both the fluid contained in the pump chamber and a portion of the fluid contained in the tank is in permanent contact with the oligodynamic substance. This is further amplified if other portions of the pump, such as the pump chamber itself, or the outlet valve, include the oligodynamic substance.

That implementation suffers from a certain number of drawbacks. Thus, depending in the nature of the fluid contained in the receptacle, permanent contact between a portion of said fluid and the oligodynamic substance can give rise to problems of stability in said fluid during storage. Secondly, manufacture of the metering pump is made more complicated and thus more expensive if one or more component parts of the pump need to include an oligodynamic substance.

Document EP-0 580 460 discloses a fluid dispenser in which the bacteriostatic substance can be provided in the pushbutton on its own. Nevertheless, in that case, the effectiveness of the bacteriostatic activity can be limited, and depending on the configuration of the component parts of the pushbutton, some of the fluid expelled during actuation runs the risk of not coming into contact with the oligodynamic substance. Similarly, if storage time is relatively short, i.e. if the dispenser is reused quickly, a portion of the fluid remaining in the pushbutton between two successive actuations runs the risk of becoming contaminated. Also, if storage time between two successive actuations is long, then a non-negligible quantity of fluid is in permanent contact with the bacteriostatic substance, and that is undesirable.

SUMMARY OF THE INVENTION

An object of the present invention is thus to provide a device for dispensing a fluid that has effective bacteriostatic activity and that avoids the risk of instability for said fluid.

Another object of the invention is to provide a fluid dispenser device having effective bacteriostatic action, in which all or nearly all of the fluid is not in permanent contact with the bacteriostatic substance.

Yet another object of the present invention is to provide a fluid dispenser device that has effective bacteriostatic activity, that is simple, and that is cheap to make.

The present invention thus provides a device for dispensing a fluid and operating without air intake, the device comprising a pump mounted on a receptacle containing the fluid, and a pushbutton for actuating said pump, said pushbutton including a fluid dispensing orifice, a substance having bacteriostatic activity on said fluid when it comes into contact with said substance being disposed in said dispenser device, said pushbutton comprising a nozzle defining an expulsion channel that is narrow and of small volume between the pump and the dispensing orifice, said substance having bacteriostatic activity being disposed solely in said pushbutton on or in the vicinity of said nozzle such that said substance having bacteriostatic activity is of maximum effectiveness because of the small dead volume in the pushbutton.

In particular, said pushbutton is a nozzle pushbutton including an internal nozzle occupying substantially the entire dead volume and defining a narrow expulsion channel, said substance having bacteriostatic activity being disposed in the expulsion channel and/or the nozzle.

In a first variant embodiment, the substance having bacteriostatic activity is incorporated in the material constituting the pushbutton and/or the nozzle.

In a second variant embodiment, the substance having bacteriostatic activity is disposed in the pushbutton and/or the nozzle in the form of a thin coating. Naturally, both variant embodiments can be combined to obtain the most effective possible bacteriostatic activity.

Advantageously, the substance having bacteriostatic activity includes ions of silver. The silver ions may, in particular, be complexed with an inorganic matrix.

Preferably, the pump is a pump that operates without air intake.

The object of the invention is to provide a fluid dispenser device having oligodynamic activity. Nevertheless, unlike the device disclosed in document EP-0 473 892, and contrary to the teaching given by that document, the pump of the invention does not include a substance having bacteriostatic or oligodynamic activity. This avoids permanent contact between the oligodynamic substance and the fluid contained in the dispenser and/or the pump chamber, and the pump is simpler and cheaper to manufacture.

On the contrary, the invention makes provision for locating a substance having bacteriostatic activity solely in the pushbutton, and not in the pump or in the receptacle. Naturally, it is preferable to use a pump that operates without air intake (commonly referred to as an "airless" pump as is well known in the state of the art) because such a pump avoids contamination of the fluid that remains in the tank after each use of the dispenser. Nevertheless, the invention is not restricted to this type of pump.

Also, contrary to the device disclosed by document EP-0 580 460, bacteriostatic activity is of maximum effectiveness because of the very small dead volume that remains in the pushbutton. This is true both during actuation of the dispenser and during storage. Because of the small dead volume there is firstly no risk of the fluid that remains in the pushbutton becoming contaminated if storage time is very short, and secondly if storage time is long there is only a very small quantity of fluid that remains in permanent contact with the bacteriostatic substance.

A particular advantage of the invention also lies in the fact that it applies to all existing pumps, in particular to airless pumps, and consequently there is no need to modify or adapt said existing pumps to obtain the desired result. In the invention, only the pushbutton needs to be modified, thus providing considerable cost savings in the manufacture of the fluid dispenser.

BRIEF DESCRIPTION OF THE DRAWING

The invention is described below in greater detail by way of non-limiting example and with reference to FIG. 1 which is a diagrammatic section view of a fluid dispenser device of the invention.

DETAILED DESCRIPTION OF THE PREFERRED EMBODIMENTS

Figure 1:
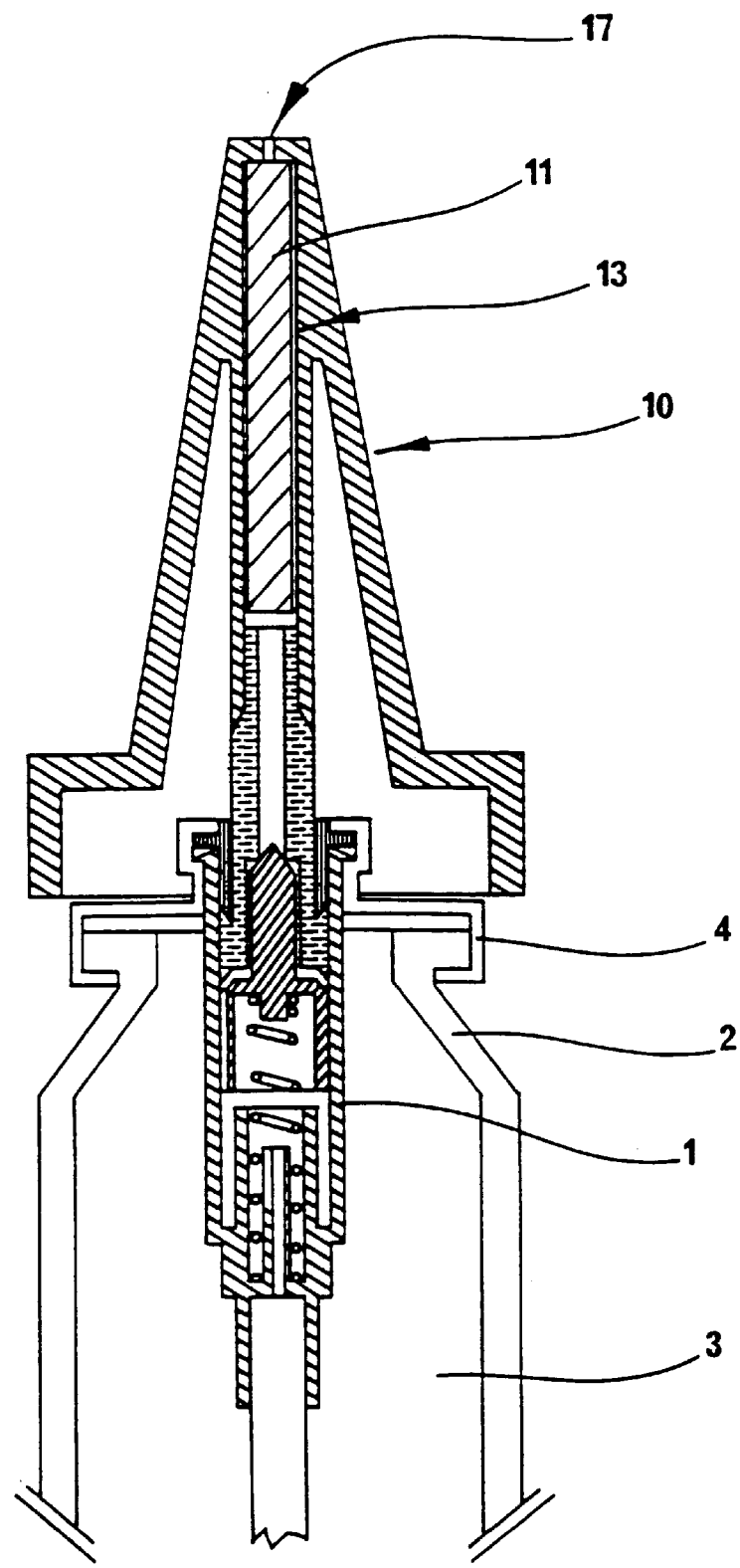

With reference to FIG. 1, the dispenser device comprises a pump 1, preferably an airless pump, of known operation which is therefore not described in greater detail below. The pump 1 is fixed to the neck 2 of a receptacle 3 in any manner, e.g. by means of a fixing ring 4. The device also includes a pushbutton 10. The pushbutton 10 has an expulsion channel 13 connecting the pump 1 to an orifice 17 for dispensing the fluid. In accordance with the invention, the pushbutton 10 includes a nozzle. Advantageously, as in the example shown in FIG. 1, the pushbutton 10 is a nasal pushbutton and includes an internal nozzle 11 disposed in the expulsion channel 13, into which the pump 1 opens out directly. The internal nozzle 11 occupies substantially all of the available volume between the pump 1 and the dispensing orifice 17, thus minimizing the dead volume. It defines an expulsion channel 13 that is very narrow and of small volume, and advantageously it enhances spraying of the fluid. Naturally, the invention applies to any other type of pushbutton including a nozzle.

In accordance with the invention, a substance having bacteriostatic activity is located solely in said pushbutton 10, on or in the vicinity of said nozzle 11. This type of bacteriostatic substance is known in the state of the art and advantageously includes heavy metals such as silver, particularly in the form of salts, e.g. nitrates or chlorides. A suitable substance is constituted, for example, by an alloy of silver chloride and titanium dioxide. Another suitable substance is constituted by silver ions complexed with an inorganic matrix.

This bacteriostatic substance can be located in one or more component portions of the pushbutton 10 that come into contact with the fluid while it is being expelled. Thus, said substance can be disposed in the expulsion channel 13. In this way, the fluid which flows along the expulsion channel 13 towards the outlet opening 17 while it is being expelled comes into contact for a short length of time only with the bacteriostatic substance, and germs contained in the fluid are eliminated. Also, between two actuations of the dispenser, because of the small dead volume, only a very small quantity of fluid remains in the pushbutton where it is in permanent contact with the bacteriostatic substance, thereby avoiding problems of stability of the fluid.

The bacteriostatic substance can be incorporated in the material constituting the pushbutton, or it may be applied in the form of a thin coating on the appropriate portions of the pushbutton 10, namely the nozzle 11 and/or the expulsion channel 13.

We claim:

1. A device for dispensing a fluid and operating without air intake, the device comprising a pump (1) mounted on a receptacle (3) containing the fluid, and a pushbutton (10) for actuating said pump, said pushbutton including a fluid dispensing orifice (17) connected to the pump via an expulsion channel (13), a substance having bacteriostatic activity on said fluid when it comes into contact with said substance being disposed in said dispenser device, wherein said pushbutton includes a nozzle (11) configured as an insert disposed in the expulsion channel and occupying substantially all available volume between the pump and the dispensing orifice so as to minimize dead volume, said substance having bacteriostatic activity being disposed exclusively in said pushbutton, and one of on the nozzle and in the vicinity of the nozzle such that said substance having bacteriostatic activity is of maximum effectiveness due to the minimized dead volume in the pushbutton.

2. A dispenser device according to claim 1, wherein said pushbutton (10) is a nozzle pushbutton including an internal nozzle (11) occupying substantially the entire dead volume and defining a narrow expulsion channel, said substance having bacteriostatic activity being disposed in the expulsion channel (13) and/or the nozzle (11).

3. A dispenser device according to claim 1, wherein the substance having bacteriostatic activity is incorporated in the material constituting one of the pushbutton and the nozzle.

4. A dispenser device according to claim 1, wherein the substance having bacteriostatic activity is disposed in one of the pushbutton and the nozzle (11) in the form of a thin coating.

5. A dispenser device according to claim 1, wherein the substance having bacteriostatic activity includes ions of silver.

6. A dispenser device according to claim 1, wherein the pump operates without air intake.

\* \* \* \* \*